United States Patent [19]

Murphy

[11] 4,149,528

[45] Apr. 17, 1979

[54] ELECTRODE ASSEMBLY FOR SENSING HEART ACTIVITY

[75] Inventor: John B. Murphy, West Roxbury, Mass.

[73] Assignee: Hewlett-Packard Company, Palo Alto, Calif.

[21] Appl. No.: 838,501

[22] Filed: Oct. 3, 1977

[51] Int. Cl.$^2$ ............................................... A61B 5/04
[52] U.S. Cl. ............................... 128/2.06 E; 128/418; 128/DIG. 4
[58] Field of Search ............... 128/2.06 E, 2.1 E, 404, 128/418, 419 P, DIG. 4

[56] References Cited

U.S. PATENT DOCUMENTS

| | | | |
|---|---|---|---|
| 3,416,534 | 12/1968 | Quinn | 128/418 |
| 3,750,650 | 8/1973 | Ruttgers | 128/2.06 E |
| 3,827,428 | 8/1974 | Hon et al. | 128/2.06 E |
| 3,986,497 | 10/1976 | Dali | 128/2.06 E |
| 4,000,745 | 1/1977 | Goldberg | 128/418 |

FOREIGN PATENT DOCUMENTS

| | | | |
|---|---|---|---|
| 1316072 | 5/1973 | United Kingdom | 128/DIG. 4 |
| 1457426 | 12/1976 | United Kingdom | 128/2.06 E |

OTHER PUBLICATIONS

Hon et al., "Electronic . . . Fetal Heart Rate", Ob. & Gyn., vol. 40, No. 3, Sep. 1972, pp. 362-365.

Primary Examiner—Lee S. Cohen
Attorney, Agent, or Firm—Stephen P. Fox

[57] ABSTRACT

An electrode assembly for sensing heart activity from body tissue includes a flexible guide tube, a spiral retaining coil disposed in one end of the guide tube, a handle disposed at the other end of the guide tube, and twisted wires inside the tube interconnecting the retaining coil and the handle. Rotation of the handle rotates the twisted wires, which in turn rotate the retaining coil to screw it into body tissue. Thereafter, the guide tube and handle are disengaged from the retaining coil and wires. A safety stop releasably disposed on the guide tube limits the rotation of the retaining coil and thus limits its depth of penetration into the body tissue.

32 Claims, 8 Drawing Figures

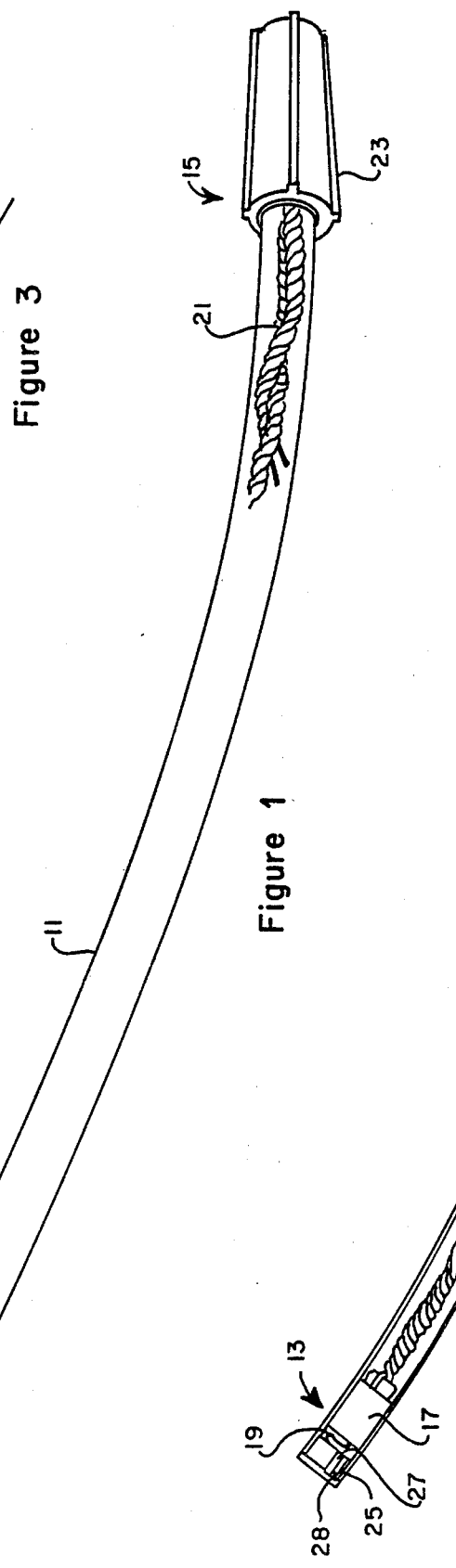
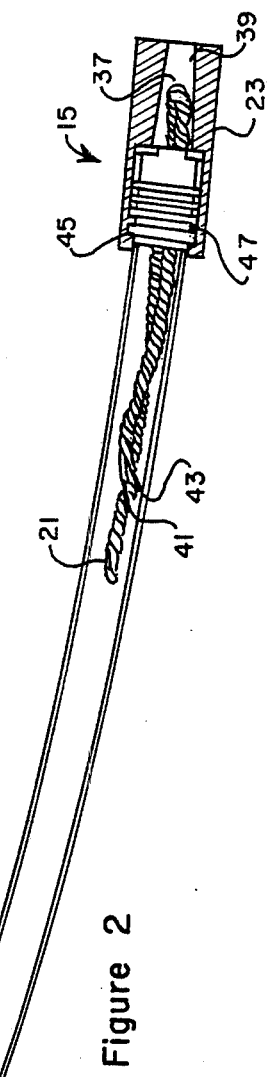

ELECTRODE ASSEMBLY FOR SENSING HEART ACTIVITY

BACKGROUND OF THE INVENTION

This invention relates generally to an electrode assembly for attachment to body tissue to sense electrical heart activity. The electrode is particularly suited for insertion through the vaginal passageway of a woman in labor and for remote controlled attachment to the fetus. The electrode provides heart signals to electronic monitoring equipment which displays an electrocardiogram and/or the heart rate.

A variety of remote controlled insertion tools and electrodes have been proposed for use in the body. For example, MacLean Pat. No. 2,839,049 describes a guide tube for insertion in the vaginal canal. The guide tube contains a wire having a handle attached to one end and a brush attached to the other end. Rotation of the handle causes rotation of the brush inside the womb.

H. D. Junge discloses an electrode for attachment to a fetus in a paper entitled "Eine Neue Technik Der Elektronischen Dauerüberwachung Von Fetaler Herzfrequenz Und Wehentätigkeit Unter Der Geburt" published in *Geburtshilfe Und Frauenheilkunde*, Feb. 1969, pages 129–133. The electrode assembly includes a retaining coil mounted on a holder. The holder is coupled to a drive rod through releasable cooperating engaging means including prongs on the rod which engage depressions on the holder. The drive rod is disposed in a guide sleeve and the assembly is inserted into the vaginal canal until the retaining coil contacts the fetus. Thereafter, the external end of the rod is rotated, thereby to rotate the retaining coil and screw it into the fetus. The guide sleeve and drive rod are then removed from the vaginal canal and a signal lead extending from the retaining coil is attached to electronic heart monitoring apparatus.

Following the publication by H. D. Junge, others developed remote controlled electrode assemblies which screw retaining coils into body tissue. Ruttgers Pat. No. 3,750,650 discloses a fetal monitoring electrode assembly including a spiral electrode extending from a holder. A drive tube retains the holder by cooperating engaging means including slots in the drive tube and projections on the holder. In use the assembly is rotated to screw the spiral electrode into an unborn fetus. The guide tube and drive tube are then telescoped to release the electrode from the tubes and the two tubes are withdrawn from the vaginal canal.

Rasor Pat. No. 3,835,864 describes a remote controlled device for screwing a retaining coil into body tissue. The coil holder is rotated by a flexible drive rod inside a guide tube. The drive rod is coupled to the coil holder through cooperating engaging means which operates to release the coil holder from the drive rod after the coil is attached to the body tissue.

Hon, et al., Pat. No. Re. 28,990 also discloses a remote controlled device for screwing a retaining coil electrode into body tissue (a fetus) wherein the coil is rotated by a drive tube inside a guide tube. The drive tube is coupled to the coil by cooperating engaging means in the form of fins on the coil holder and slots in the drive tube.

One disadvantage inherent in electrode assemblies of the type described above is that they are characterized by complex insertion tool arrangements. Numerous components including guiding and driving tubes and releasable cooperating engaging means are required to achieve remote controlled rotation to screw the electrode coil into body tissue. These complex configurations are costly to manufacture and are often difficult to satisfactorily manipulate in use.

Another disadvantage of heretofore known electrode assemblies relates to the manner in which the electrode coil is applied to the body tissue. The retaining coil itself is usually small and formed with a few turns of sharply pointed stanless steel wire. When the coil is manually rotated by the insertion tool mechanism, it can easily be screwed deeply into body tissue. There is a danger that the electrode may be manually overdriven with consequent tearing of the tissue. In the case where the electrode coil is a few millimeters in diameter and applied through the vaginal canal to a fetus, the large torque transmitted by the insertion tool may drive the coil so deeply and tightly into the fetus that a plug of flesh is pulled out. Such coring by the electrode coil is traumatic to the fetus and precludes satisfactory electrode attachment for sensing heart activity.

SUMMARY OF THE INVENTION

The present invention provides a simplified electrode assembly which permits remote controlled rotation of an electrode coil without the aforementioned complex arrangement of guiding and driving tubes and releasable cooperating engaging means coupling the driving tube to an electrode holder. In addition, the present invention provides an electrode assembly in which the electrode coil penetration of the head of a fetus or other body tissue is limited to safe depths, on the order of a few millimeters, without danger of driving the coil too deeply or tightly into the body tissue.

The illustrated embodiment of the invention includes a flexible guide tube having a proximal end positionable adjacent to body tissue and a distal end remote from the body tissue. Disposed in the guide tube at the proximal end is a spiral retaining coil mounted on an electrode holder. Two twisted signal leads extend from the electrode holder through the guide tube to the distal end thereof. A rotatable handle on the distal end releasably engages the twisted signal leads. Rotation of the handle rotates the signal leads which in turn rotate the spiral retaining coil to screw it into body tissue. A safety stop at the proximal end of the guide tube engages the spiral retaining coil and limits rotation of the coil, thereby to limit its depth of penetration into the body tissue. Following attachment of the retaining coil to the body tissue, the guide tube is pulled off the signal leads which are then coupled to suitable electronic heart monitoring equipment.

BRIEF DESCRIPTION OF THE DRAWINGS

FIG. 1 is a perspective view of one embodiment of the electrode assembly of the present invention.

FIG. 2 is a longitudinal cross-sectional view of the electrode assembly.

FIG. 3 is an enlarged perspective view of a portion of one end of the electrode assembly.

DESCRIPTION OF THE PREFERRED EMBODIMENT

Figure 4A:
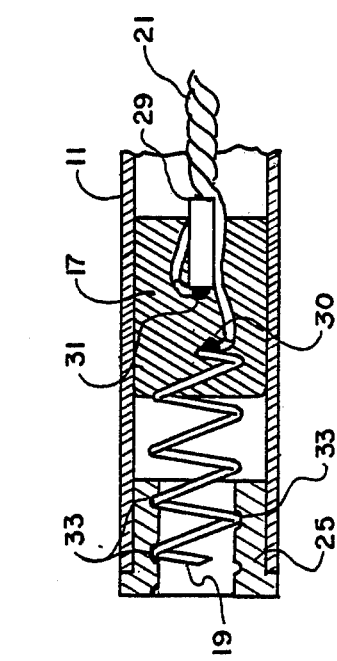
FIG. 4(*a*) and 4(*b*) are enlarged cross-sectional views of one end of the electrode assembly.

Referring now to FIG. 1 there is shown an electrode assembly including a guide tube 11 having a proximal end 13 positionable against a fetus or other body tissue, and a remote distal end 15. the guide tube 11 is preferrably constructed of a flexible plastic, such as polyethylene, and typically has an outside diameter on the order of eight millimeters. The flexible guide tube 11 is formed with a slight bend in it to facilitate insertion into body cavities, such as the vaginal passageway.

Disposed in guide tube 11 at the proximal end 13 is a rotatable electrode holder 17. Mounted on holder 17 is a spiral retaining coil 19 which is extendable from proximal end 13. A pair of twisted vinyl insulated wires 21 are attached to holder 17 and extend through guide tube 11 to the distal end 15. A handle 23 is mounted on the distal end 15 of the guide tube and coupled to the twisted wires 21. Rotation of handle 23 causes rotation of the wires 21, which in turn act as a drive member to rotate holder 17. The rotation of holder 17 rotates the spiral retaining coil 19 mounted thereon to extend from proximal end 13 and screw the coil into the body tissue, as hereinafter described.

Disposed at the proximal end 13 of the guide tube is a safety stop 25 which is in the form of a ring having internal threads for receiving the spiral retaining coil 19. The spiral coil 18 is threaded into ring 25. Rotation of the holder 17 causes retaining coil 19 to be screwed through ring 25 and to extend beyond the ring. Ring 25 limits the extension of retaining coil 19 from the proximal end 13 of the guide tube by limiting the rotation of the coil, as described below.

FIG. 2 illustrates the electrode assembly in cross-section. At the proximal end 13, the safety stop ring 25 is releasably disposed in the end of guide tube 11. More particularly, as shown in FIG. 3, the end of the guide tube includes one or more slots 27 which engage protrusions 28 on the ring 25. Ring 25 may be disengaged from guide tube 11 by sliding it away from the guide tube along the longitudinal axis thereof.

Figure 4B:
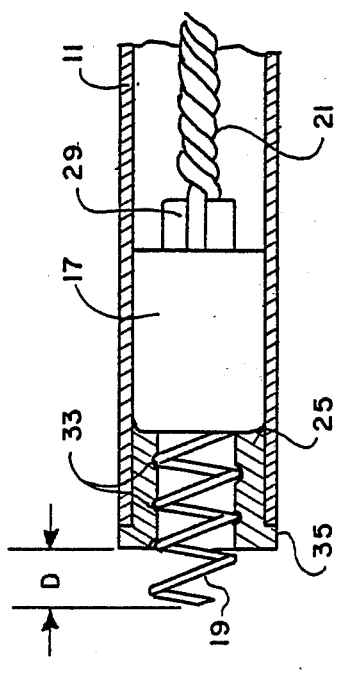

FIGS. 4(a) and 4(b) are enlarged cross-sectional views of the proximal end 13 of the electrode assembly. With reference to the cross-section of holder 17 in FIG. 4(a), one of the two twisted wires 21 is connected to the end of spiral retaining coil 19 internally of holder 17 at point 30. The retaining coil 19 extends from a forward end surface of holder 18 toward the open end of the guide tube. On the rearward end surface of holder 17 there is mounted a plate-like electrode 29 which is connected to the other one of the twisted wires 21 at point 31. Thus, the two twisted wires 21 serve as electrical signal leads. The spiral retaining coil 19 functions as a first electrode, and the rearwardly extending plate 29 functions as a second electrode.

Holder 17 has a cylindrical configuration with an outside diameter which is slightly less than the inside diameter of guide tube 11, thereby to permit the holder to be rotated inside the guide tube by the torque applied to the signal lead wires 21. Ring 25 has internal threads 33 which have substantially the same pitch as the pitch of the spiral retaining coil 19. As holder 17 is rotated, retaining coil 19 is screwed into the threaded ring 25 until the forward end surface of holder 17 abuts the rearward end surface of ring 25, as shown in FIG. 4(b). The engagement of holder 17 with ring 25 terminates the rotation of the holder and thus limits the forward advancement of retaining coil 19 through the ring 25.

FIG. 4(b) illustrates holder 17 shifted 90 degrees from the position shown in FIG. 4(a), thereby to illustrate the side and top of plate 29 which forms the second electrode.

The spiral retaining coil 19 has a predetermined length along its longitudinal axis, so as to permit the retaining coil to pass through ring 25 and extend beyond it a predetermined distance D. In the case where the retaining coil 19 is screwed into the head of a fetus, the dimension D is preferably on the order of two millimeters. By limiting the rotation of holder 17 and the forward advancement of retaining coil 19 out of the end of guide tube 11, the ring 25 acts as a safety stop. The penetration of spiral retaining coil 19 into the fetus or other body tissue is limited to safe depths. There is no danger that the coil will be driven too deeply and tightly into the body tissue. Nor is there any risk of tearing or coring the body tissue by over-driving the spiral retaining coil.

While holder 17 is screwed into ring 25, the ring is held against axial rotation by the protrusion 28 thereon which engages slot 27 in the guide tube 11 (see FIGS. 2 and 3). As shown in FIG. 4(b), ring 25 includes a flange 35 which abuts against the proximal end of guide tube 11 to assist in holding the ring 25 in position at the end of the guide tube. The assembly of ring 25 and holder 17 may be slid out of the guide tube, as described hereinafter.

Figure 5:
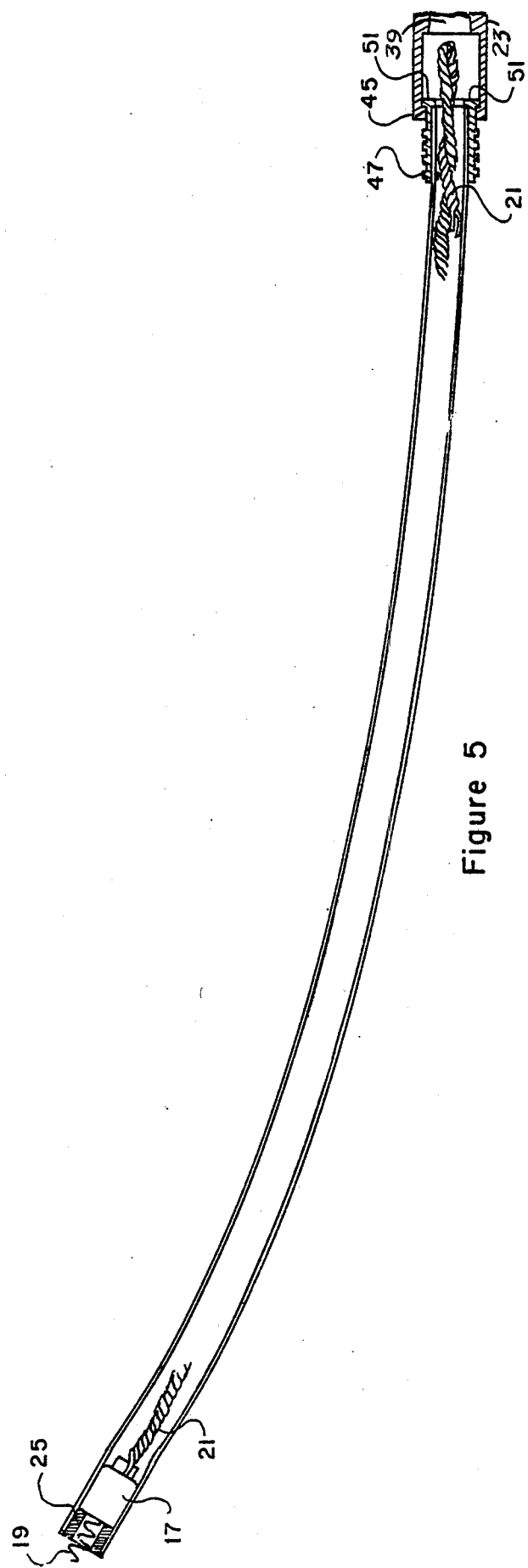
FIG. 5 is another longitudinal cross-sectional view of the electrode assembly.

With reference to FIGS. 2 and 5, rotation of the spiral retaining coil is achieved by rotating the handle 23 at the distal end of guide tube 11. FIG. 2 illustrates the electrode assembly before use, wherein the retaining coil 19 is only partially screwed into the ring 25. FIG. 5 illustrates the electrode assembly after the retaining coil 19 has been screwed into ring 25 until holder 17 abuts ring 25, thereby limiting further rotation.

As shown in FIG. 2, the twisted signal leads extend from the rear surface of holder 17 to the distal end 15 of the guide tube. At the distal end, the two twisted signal leads are folded back on themselves at point 37 and received by a slot 39 in the rearward portion of handle 23. The folded signal wires 21 return back up into guide tube 11 and terminate in two bare electrical conductor wires 41, 43.

Handle 23 shown in FIG. 5 is rotated 90 degrees from its position shown in FIG. 2. It can be seen that slot 39 has a tapered rectangular shape. The slot is dimensioned to firmly hold the looped portion of wires 21 in longitudinally slidable engagement therewith. Rotation of the handle 23 about its longitudinal axis will rotate the looped end of wires 21 and thus impart rotational motion to the wires 21 in guide tube 11.

Handle 23 includes an internally threaded cylindrical end portion 45 which threadedly engages an externally threaded collar 47 firmly affixed to the distal end of guide tube 11. The threads on handle 23 and collar 47 are of the "left-hand" type, so that rotation of the handle in a clock-wise direction on collar 47 serves to unscrew the handle from the collar. As the handle 23 is unscrewed from collar 47, slot 39 moves away from the looped end of wires 21 until the wires are disengaged from the slot. Following such disengagement, continued rotation of handle 23 will not rotate wires 21. After handle 23 is unscrewed from the threads on collar 47, the handle is freely rotatable on the distal end of guide tube and held onto the distal end by a plurality of protrusions 51 surrounding the circumference of the rearward end of collar 47.

The operation of the electrode assembly may be understood by reference to FIGS. 2 and 5. Initially, as shown in FIG. 2, the spiral retaining coil 19 is screwed partway into ring 25 and the tip of the coil is recessed from the end of the ring. Ring 25 and holder 17 are disposed in spaced apart relation, separated by a few turns of the retaining coil 19. At the distal end 15 of guide tube 11, handle 23 is threaded all of the way onto collar 47 and the folded wires 21 are inserted fully into slot 39. In use, handle 23 is manually rotated to impart torque to the wires 21, which in turn rotates holder 17 and screws the spiral retaining coil 19 into ring 25. After a few turns of handle 23, holder 17 stops against ring 25, as shown in FIG. 5. At this point, spiral retaining coil 19 extends a predetermined distance from the end of ring 25 and will not rotate further. Continued rotation of handle 23 will merely twist wires 21 more tightly while longitudinally displacing the handle on the threaded collar 47. Ultimately the folded end of wires 21 disengages slot 39 in the handle and continued twisting of the wires ceases. Handle 23 becomes freewheeling at the distal end. It can be seen that the safety stop in the form of ring 25 at the proximal end 13 limits the extension of spiral retaining coil 19, while the automatic disengagement of the handle 23 from the looped wires 21 with continued rotation of the handle terminates the application of torque to holder 17 and prevents the assembly from being over driven by excessive manual force.

Figure 6:
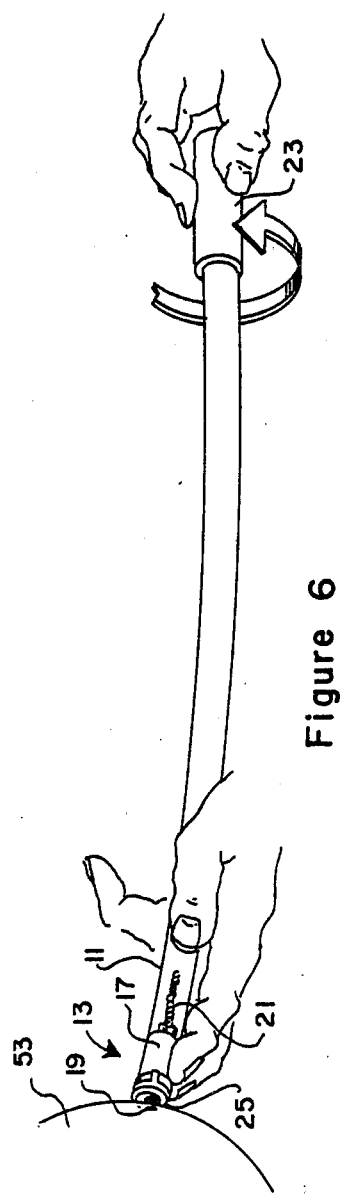
FIG. 6 is a perspective view illustrating use of the electrode assembly in attaching the electrode to body tissue.
Figure 7:
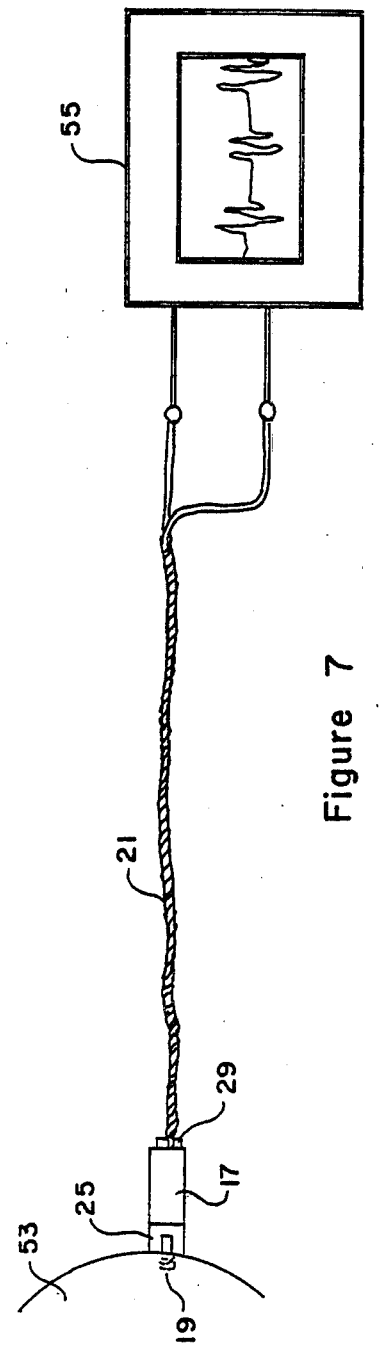
FIG. 7 is a diagramatic view illustrating use of the electrode with an electronic heart monitoring instrument.

FIG. 6 illustrates the electrode assembly as it is applied to body tissue before use in sensing heart activity. Body tissue 53 may be, for example, the head of a fetus or other fetal presenting part encountered by a doctor prior to delivery. Initially, the doctor applies the proximal end 13 of the assembly to the body tissue. Typically, the first two fingers of the left-hand are used to guide the proximal end 13 to make contact with the appropriate part of the body tissue 53. After contact is made, the doctor rotates handle 23 with his right-hand to screw spiral retaining coil 19 out of ring 25 and into the body tissue 53. After retaining coil 19 penetrates the body tissue to the permissible limit, as determined by the length of the coil 19 and the abutment of ring 25 with the coil holder 17 and after disengagement of the folded wires 21 at the distal end 15 from slot 39 in handle 23, the doctor pulls the guide tube 11 away from the body tissue 53, thereby to slide the guide tube off of ring 25, holder 17 and the attached wires 21. Thereafter the exposed twisted wires 21 are unfolded at the distal end 15 and connected to a suitable monitoring instrument 55 as shown in FIG. 7. In the case where body tissue 53 is the head of a fetus, the spiral retaining coil 19 and the rearwardly extending plate 29 act as first and second bipolar electrodes, respectively, to sense fetal heart activity. The monitoring instrument 55 displays the fetal electrocardiogram and/or the fetal heart rate.

After application of the spiral retaining coil 19, the guide tube 11 and attached handle 23 may be discarded. Also, after use of the electrode for monitoring heart activity, the spiral retaining coil 19 is unscrewed from body tissue 53 by holding the ring 25 in one hand and rotating holder 17 counterclockwise with the other hand. Thereafter, the coil and holder assembly and attached wires may also be discarded.

I claim:

1. An electrode assembly for sensing heart activity from body tissue comprising:
    a guide tube having proximal and distal ends;
    an electrically conductive spiral retaining coil disposed in the proximal end of said guide tube and extendable from the proximal end;
    a signal lead attached to said retaining coil and extending through said guide tube to the distal end thereof said signal lead being folded back on itself at said distal end; and
    a handle rotatably disposed at the distal end of said guide tube, said handle including a slot releasably engaging the folded end of said signal lead.

2. The apparatus of claim 1 wherein said handle threadedly engages the distal end of said guide tube thereby to permit displacement of said handle from said guide tube along the longitudinal axis of said guide tube by rotation of said handle.

3. The apparatus of claim 2 wherein the slot in said handle is disposed on the longitudinal axis of said folded signal lead, thereby to permit longitudinal disengagement of the folded end of said signal lead from said slot by rotation of said handle.

4. The apparatus of claim 2 further including an externally threaded collar attached to the distal end of said guide tube and wherein said handle has an internally threaded portion engaging said threaded collar.

5. The apparatus of claim 1 further including:
    a holder disposed in said guide tube at the proximal end thereof and holding said spiral retaining coil;
    an electrode mounted on said holder; and
    a signal lead attached to the electrode on said holder and extending through said guide tube to the distal end thereof;
    wherein the signal leads attached to said retaining coil and to said electrode are twisted together inside said guide tube.

6. The apparatus of claim 1, further including:
    a holder disposed in said guide tube at the proximal end thereof and holding said spiral retaining coil; and
    a safety stop disposed at the proximal end of said guide tube and including a portion within said proximal end of said guide tube and engagable with said holder upon predetermined rotation of said retaining coil to terminate the rotation of said coil into said body tissue.

7. An electrode assembly for sensing heart activity from body tissue comprising:
    a guide tube having proximal and distal ends;
    an electrically conductive spiral retaining coil disposed in the proximal end of said guide tube and extendable from the proximal end;
    a ring releasably disposed on the proximal end of said guide tube, said ring having an internal thread engaging said spiral retaining coil, thereby to permit said retaining coil to be screwed into said ring;
    a signal lead attached to said retaining coil and extending through said guide tube to the distal end thereof; and
    a handle rotatably disposed at the distal end of said guide tube in engagement with said signal lead to rotate said retaining coil by rotating said signal lead.

8. The apparatus of claim 7 wherein the pitch of the internal thread in said ring is the same as the pitch of said spiral retaining coil.

9. The apparatus of claim 37 further including a holder disposed in said guide tube at the proximal end thereof and holding said spiral retaining coil, said holder having a surface portion abuttable with said ring to limit the advancement of said retaining coil into said ring.

10. The apparatus of claim 9 wherein said retaining coil has a predetermined length along a longitudinal axis thereof to permit said retaining coil to pass through said ring and extend beyond said ring a predetermined distance.

11. The apparatus of claim 9 wherein said spiral retaining coil is a first electrode on said holder; and further including a second electrode mounted on said holder and a signal lead attached to said second electrode and extending through said guide tube to the distal end thereof.

12. The apparatus of claim 11 wherein said spiral retaining coil extends from a forward end surface of said holder facing the proximal end of said guide tube and said second electrode extends from a rearward end surface of said holder facing the distal end of said guide tube.

13. The apparatus of claim 11 wherein said signal leads attached respectively to said retaining coil and to said second electrode are twisted together.

14. The apparatus of claim 7 wherein said ring is disposed in said guide tube and slidably removable therefrom along the longitudinal axis thereof.

15. The apparatus of claim 14, said ring having a protrusion thereon and the proximal end of said guide tube having a slot therein slidably engaging said protrusion.

16. The apparatus of claim 14, said ring including a flange abutting the proximal end of said guide tube.

17. An electrode apparatus for sensing heart activity from body tissue comprising:
  a guide tube having proximal and distal ends;
  a rotatable electrode assembly including a holder disposed in said guide tube at the proximal end thereof, and an electrically conductive spiral retaining coil mounted on said holder and extending toward the proximal end of said guide tube;
  a signal lead attached to said retaining coil;
  a rotatable drive member coupled to said holder and extending through said guide tube to the distal end thereof;
  a handle disposed at the distal end of said guide tube and coupled to said drive member for rotating said drive member to rotate said holder and the spiral retaining coil mounted thereon; and
  a safety stop disposed at the proximal end of said guide tube and including a portion within said proximal end of said guide tube and engagable with said electrode assembly upon predetermined rotation of said electrode assembly to terminate rotation of said retaining coil into said body tissue.

18. The apparatus of claim 17 wherein said safety stop including said portion includes an internally threaded ring releasably disposed on the proximal end of said guide tube; said holder having an external diameter greater than the internal diameter of the threaded portion of said ring; and said retaining coil engaging the threads of said ring and being limited in advancement through said ring by said holder abutting said ring.

19. The apparatus of claim 18 wherein the pitch of the internal thread in said ring is the same as the pitch of said spiral retaining coil.

20. The apparatus of claim 18 wherein said retaining coil has a predetermined length to extend beyond said ring a predetermined distance when said holder abuts said ring.

21. The apparatus of claim 18 wherein said ring is disposed in said guide tube and slidably removable therefrom along the longitudinal axis thereof.

22. The apparatus of claim 21, said ring having a protrusion thereon, and the proximal end of said guide tube having a slot therein engaging said protrusion.

23. The apparatus of claim 21 said ring including a flange abutting the proximal end of said guide tube.

24. The apparatus of claim 17 wherein said spiral retaining coil is one electrode on said holder; and further including a second electrode mounted on said holder and a signal lead attached to said second electrode.

25. The apparatus of claim 24 wherein said retaining coil extends from a forward end surface of said holder facing the proximal end of said guide tube and said second electrode extends from a rearward end surface of said holder facing the distal end of said guide tube.

26. An electrode apparatus for sensing heart activity from body tissue comprising:
  a guide tube having proximal and distal ends;
  a rotatable electrode assembly including a holder disposed in said guide tube at the proximal end thereof, and two electrode elements disposed on said holder, one of said electrode elements being an electrically conductive spiral retaining coil extending toward the proximal end of said guide tube;
  a pair of rotatable torque-transmitting twisted wires attached to said holder to rotate said retaining coil disposed thereon, said wires extending through said guide tube to the distal end thereof, said twisted wires being signal leads electrically coupled to said two electrode elements, respectively; and
  a handle rotatably disposed at the distal end of said guide tube, said handle being in engagement with said twisted wires, said handle being coupled to apply torque to said twisted wires to rotate said holder by rotating said wires and screw said spiral retaining coil into body tissue.

27. The apparatus of claim 26 further including a safety stop disposed at the proximal end of said guide tube and including a portion within said proximal end of said guide tube and engagable with said electrode assembly upon predetermined rotation of said electrode assembly to terminate the rotation of said spiral retaining coil into said body tissue.

28. The apparatus of claim 27 wherein said safety stop including said portion includes an internally threaded ring releasably disposed on the proximal end of said guide tube; said holder having an external diameter greater than the internal diameter of the threaded portion of said ring; and said retaining coil engaging the threads of said ring and being limited in advancement through said ring by said holder abutting said ring.

29. The apparatus of claim 28 wherein said retaining coil has a predetermined length to extend beyond said ring a predetermined distance when said holder abuts said ring.

30. The apparatus of claim 26, said handle having a slot therein releasably engaging said twisted wires.

31. The apparatus of claim 30 wherein said twisted wires are folded back on themselves at the distal end of said guide tube, the folded end of said wires being disposed in the slot of said handle.

32. The apparatus of claim 31 wherein said handle is movable along the longitudinal axis of said guide tube and wherein the slot in said handle engaging said wires is disposed on said longitudinal axis, thereby to permit longitudinal disengagement of the said wires from said slot by moving said handle.

* * * * *

UNITED STATES PATENT AND TRADEMARK OFFICE
CERTIFICATE OF CORRECTION

PATENT NO. : 4,149,528
DATED : April 17, 1979
INVENTOR(S) : John B. Murphy

It is certified that error appears in the above–identified patent and that said Letters Patent are hereby corrected as shown below:

Column 3, line 10, cancel "the" and substitute -- The --;

Column 3, line 32, cancel "18" and substitute -- 19 --;

Column 3, line 52, cancel "18" and substitute -- 17 --;

Column 5, line 32, cancel "force." and substitute -- forces. --;

Column 7, line 1, cancel "37" and substitute -- 7 --;

Signed and Sealed this

Fifth Day of February 1980

[SEAL]

Attest:

SIDNEY A. DIAMOND

Attesting Officer     Commissioner of Patents and Trademarks